United States Patent [19]
Takikawa et al.

[11] Patent Number: 5,648,612
[45] Date of Patent: Jul. 15, 1997

[54] METHOD OF MEASURING CAVITIES IN FORMED PRODUCT FORMED BY SUPERPLASTIC FORMING

[75] Inventors: Isao Takikawa; Tadao Kanno, both of Saitama-ken, Japan

[73] Assignee: Honda Giken Kogyo Kabushiki Kaisha, Tokyo, Japan

[21] Appl. No.: 594,760

[22] Filed: Jan. 31, 1996

[30] Foreign Application Priority Data

Feb. 6, 1995 [JP] Japan ................................. 7-018063

[51] Int. Cl.$^6$ ............................................. G01N 29/18
[52] U.S. Cl. ............................................. 73/598; 73/629
[58] Field of Search ........................... 73/598, 597, 615, 73/616, 629

[56] References Cited

U.S. PATENT DOCUMENTS 4,407,682  10/1983  Sawa et al. ........................ 148/564
4,896,278  1/1990   Grove .................................. 73/598
5,533,411  7/1996   Koiwa ................................. 73/598

*Primary Examiner*—John E. Chapman
*Attorney, Agent, or Firm*—Armstrong, Westerman, Hattori, McLeland & Naughton

[57] ABSTRACT

The concentration of cavities in a formed product formed by superplastic forming is measured based on a propagation velocity of ultrasonic waves in the formed product. An ultrasonic measuring head which oscillates and receives ultrasonic waves is brought into contact with the formed product. A measurement is made of the propagation time required for the ultrasonic waves to be incident from the ultrasonic measuring head on the formed product to return to the ultrasonic measuring head upon reflection from a rear surface of the formed product. The propagation velocity is obtained from the measured propagation time and the thickness of the formed product.

3 Claims, 1 Drawing Sheet

METHOD OF MEASURING CAVITIES IN FORMED PRODUCT FORMED BY SUPERPLASTIC FORMING

BACKGROUND OF THE INVENTION

1. Field of the Invention

The present invention relates to a method of measuring the concentration of cavities (small pores) which occur in a formed product which is formed or processed by superplastic forming.

2. Description of the Related Art

It is conventionally known to form or manufacture products of complicated configurations by superplastic forming with aluminum-based materials or titanium-based materials. However, when these materials are subjected to superplastic forming, cavities are likely to occur due to metallic grain boundary sliding, with the result that the strength of the formed products is decreased.

As a solution, the quality control of the formed products is conventionally carried out by cutting samples of the formed products and measuring the concentration of cavities through a microscopic observation (i.e., by using a microscope).

However, it is impossible in the above-described destructive test to measure the concentration of cavities in all of the formed products. It is therefore desirable to measure the concentration of cavities in a nondestructive method in order to secure the quality of the formed products.

SUMMARY OF THE INVENTION

The present invention has an object of providing such a method of measuring the concentration of cavities of the formed products formed by superplastic forming which will meet the above-described desire.

In order to attain the above object, the present invention is a method of measuring a concentration of cavities in a formed product formed by superplastic forming, comprising the step of measuring the concentration of cavities based on a propagation velocity of ultrasonic waves in the formed product.

Preferably, the method further comprises the steps of: contacting an ultrasonic measuring head, which oscillates and receives ultrasonic waves, with the formed product; measuring a propagation time required for the ultrasonic waves to be incident from the ultrasonic measuring head on the formed product to return to the ultrasonic measuring head upon reflection from a rear surface of the formed product; and obtaining a propagation velocity from the measured propagation time and a thickness of the formed product.

The method preferably uses an ultrasonic thickness meter having an ultrasonic measuring head which oscillates and receives ultrasonic waves. The method then further comprises the steps of: contacting the ultrasonic measuring head with the formed product; measuring a propagation time required for the ultrasonic waves to be incident from the ultrasonic measuring head on the formed product to return to the ultrasonic measuring head upon reflection from a rear surface of the formed product; and measuring the concentration of cavities by comparing a measured thickness value of the formed product and an actual thickness of the formed product, said measured thickness value being obtained from the measured propagation time and a propagation velocity reference value to be determined by a material of the formed product.

Let the propagation velocity of the ultrasonic waves be $V$, the Young's modulus and the density of the medium for propagation be $E$ and $\rho$, respectively. Then, the following formula can be established.

$$V \propto \sqrt{E/\rho}$$

The Young's modulus $E$ and the density $\rho$ of the formed product, which is the medium for propagation, vary with the concentration of the cavities in the formed product, and a predetermined correlation is established between the amount of cavities and the propagation velocity $V$ of the ultrasonic waves. Therefore, the concentration of cavities can be measured from the propagation velocity $V$.

BRIEF DESCRIPTION OF THE DRAWINGS

The above and other objects and the attendant advantages of the present invention will become readily apparent by reference to the following detailed description when considered in conjunction with the accompanying drawings wherein.

DETAILED DESCRIPTION OF A PREFERRED EMBODIMENT

Figure 1:
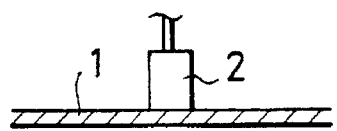
FIG. 1 is a diagram showing the condition of inspecting the formed product formed by superplastic forming.

Referring to FIG. 1, reference numeral 1 denotes a formed product formed by superplastic forming. An ultrasonic measuring head 2 for oscillating and receiving ultrasonic waves is placed in contact with the surface of the formed product 1. Then, a measurement is made of the propagation time T that is required for the ultrasonic waves incident from the ultrasonic measuring head 2 placed upon the formed product 1 to return to the measuring head 2 upon reflection from the rear surface of the formed product 1.

The propagation velocity $V$ of the ultrasonic waves in the formed product 1 can be obtained from the thickness D of the formed product 1 and the propagation time T by the following formula:

$$V = 2D/T$$

Since the thickness D of the formed product 1 can be easily managed or controlled, it is not always necessary to measure it for each formed product. However, whenever there is a possibility that the thickness D fluctuates, the thickness D is measured by means of a mechanical measuring means such as a micrometer or the like, thereby obtaining the propagation velocity $V$.

Figure 2:
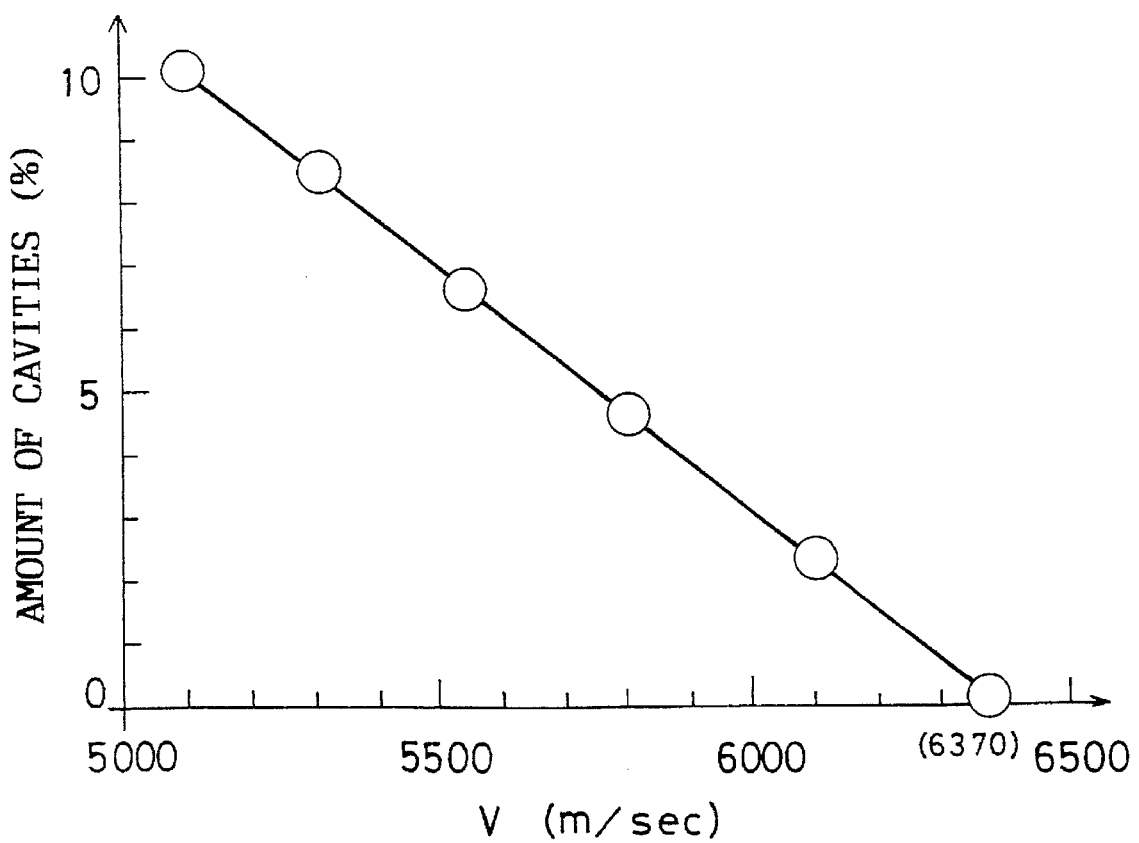
FIG. 2 is a graph showing the relationship between the propagation velocity of ultrasonic waves and the concentration of cavities.

A plurality of test pieces were manufactured by superplastic forming under different conditions. The propagation velocity $V$ of the ultrasonic waves in these test pieces was measured. The test pieces were cut to measure the concentration of cavities (the area represented in % of the cavities in the cross-sectional area) was measured through a microscopic observation (i.e., measured with a microscope). The results of the observation are shown in FIG. 2. The material of the test pieces was an aluminum-based superplastic forming material whose main composition was aluminum (Al), with 0.04% of silicon (Si), 0.05% of iron (Fe), 0.02% of copper (Cu), 4.53% of manganese (Mn), 0.12% of chromium (Cr), 0.01% of titanium (Ti) and unavoidable impurities. The frequency of the ultrasonic waves was 15 MHz.

As can be seen from FIG. 2, it has been found that a linear relation can be established between the propagation velocity V and the concentration of cavities and, therefore, that the concentration of cavities can be measured from the propagation time T.

The concentration of cavities can also be measured based on a parameter which has a predetermined correlation with the propagation velocity V, e.g., an apparent value of the thickness (also called "an apparent thickness value") of an ultrasonic thickness meter which has a measuring head similar to that in the above-described measuring head 2 and which measures the apparent thickness of an object of measurement from the propagation time T and a known propagation velocity to be determined by the material of the object for measurement. The measurement of the concentration of cavities in the present invention also includes the measurement based on this kind of parameter. When the ultrasonic thickness meter is used, the apparent thickness of the formed product is measured by a propagation velocity reference value determined by the material of the formed product and the propagation time. This measured thickness value and the actual thickness of the formed product are compared to thereby measure the concentration of cavities.

As can be seen from the above-described explanations, according to the present invention, the concentration of cavities in the product formed by superplastic forming can be measured in a nondestructive method. It therefore becomes possible to measure all of the formed products, with the result that the quality of the formed products can be improved.

It is readily apparent that the above-described method of measuring the cavities in a formed product formed by superplastic forming meets all of the objects mentioned above and also has the advantage of wide commercial utility. It should be understood that the specific form of the invention hereinabove described is intended to be representative only, as certain modifications within the scope of these teachings will be apparent to those skilled in the art.

Accordingly, reference should be made to the following claims in determining the full scope of the invention.

What is claimed is:

1. A method of measuring a concentration of cavities in a formed product formed by superplastic forming based on a propagation velocity of ultrasonic waves in the formed product comprising the steps of:

propagating ultrasonic waves in the formed product;

measuring the propagation velocity of the ultrasonic waves; and determining the concentration of cavities based on the measured propagation velocity.

2. A method of measuring a concentration of cavities in a formed product formed by superplastic forming according to claim 1, further comprising the steps of:

contacting an ultrasonic measuring head, which oscillates and receives ultrasonic waves, with the formed product;

measuring a propagation time required for the ultrasonic waves to be incident from the ultrasonic measuring head on the formed product to return to the ultrasonic measuring head upon reflection from a rear surface of the formed product; and obtaining said propagation velocity from the measured propagation time and a thickness of the formed product.

3. A method of measuring a concentration of cavities in a product formed by superplastic forming, wherein an ultrasonic thickness meter having an ultrasonic measuring head which oscillates and receives ultrasonic waves is used, comprising the steps of:

contacting the ultrasonic measuring head with the formed product;

measuring a propagation time required for the ultrasonic waves to be incident from the ultrasonic measuring head on the formed product to return to the ultrasonic measuring head upon reflection from a rear surface of the formed product; and measuring the concentration of cavities by comparing an apparent thickness value of the formed product and an actual thickness of the formed product, said apparent thickness value being obtained from said measured propagation time and a propagation velocity reference value determined by a material of the formed product.

* * * * *